United States Patent
Tomioka et al.

(10) Patent No.: US 7,041,306 B2
(45) Date of Patent: May 9, 2006

(54) INSECT PEST-REPELLENT FILM, INSECT PEST-REPELLENT PAINT AND METHOD FOR PRODUCING THE SAME

(75) Inventors: Toshikazu Tomioka, Ibaraki (JP); Toshihiko Nukui, Neyagawa (JP); Akira Kitawaki, HigashiOsaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 10/129,943

(22) PCT Filed: Sep. 10, 2001

(86) PCT No.: PCT/JP01/07818

§ 371 (c)(1),
(2), (4) Date: Sep. 6, 2002

(87) PCT Pub. No.: WO02/22753

PCT Pub. Date: Mar. 21, 2002

(65) Prior Publication Data

US 2003/0049297 A1    Mar. 13, 2003

(30) Foreign Application Priority Data

Sep. 11, 2000  (JP)  ............... 2000-274637
Jul. 27, 2001  (JP)  ............... 2001-227454

(51) Int. Cl.
*A01N 25/32* (2006.01)

(52) U.S. Cl. .................... 424/406; 43/112; 43/113; 424/405; 424/407; 424/409; 424/421; 514/521

(58) Field of Classification Search ............... 424/400, 424/405–407, 409, 411–420, 421; 43/112, 43/113; 514/63, 519, 521, 531
See application file for complete search history.

(56) References Cited

U.S. PATENT DOCUMENTS

| 3,808,264 | A | * | 4/1974 | Peterson et al. ............... 549/3 |
| 4,927,465 | A | * | 5/1990 | Hyder et al. ................ 106/486 |
| 5,505,017 | A | * | 4/1996 | Nelson et al. ................ 43/113 |
| 5,730,996 | A | * | 3/1998 | Beall et al. ................ 424/405 |
| 6,358,520 | B1 | * | 3/2002 | Lo et al. .................... 424/408 |

FOREIGN PATENT DOCUMENTS

EP    0 859 035    8/1998

(Continued)

OTHER PUBLICATIONS

European Search Report for Application No. EP. 01 96 5561 dated Jan. 21, 2003.

(Continued)

*Primary Examiner*—Neil S. Levy
(74) *Attorney, Agent, or Firm*—RatnerPrestia

(57) ABSTRACT

Insects come into lighting fixtures, and enormous efforts are expended to clean the interior of a glove. Here is provided a repellent paint, which prevents this effect.

The repellent paint is characterized in that it has at least cyclopropane carboxylate as a repellent ingredient, and comprises at least a porous carrier particle of an inorganic oxide, a surfactant, a paint binder and a solvent.

5 Claims, 1 Drawing Sheet

FOREIGN PATENT DOCUMENTS

| | | |
|---|---|---|
| EP | 0 953 611 | 11/1999 |
| JP | 61-127742 | 6/1986 |
| JP | 63-284276 | 11/1988 |
| JP | 4-74101 | 3/1992 |
| JP | 04-370177 | 12/1992 |
| JP | 06-03299 | 2/1994 |
| JP | 10-17846 | 1/1998 |
| JP | 10-286914 | 10/1998 |
| JP | 10-316507 | 12/1998 |
| JP | 2000-319104 | 11/2000 |
| WO | WO89/03863 * | 5/1989 |

OTHER PUBLICATIONS

International Search Report corresponding to application No. PCT/JP01/07818 dated Jan. 15, 2002.

English Translation of Form PCT/ISA/210.

* cited by examiner

INSECT PEST-REPELLENT FILM, INSECT PEST-REPELLENT PAINT AND METHOD FOR PRODUCING THE SAME

This application is U.S. National Phase Application of PCT International Application PCT/JP01/07818.

TECHNICAL FIELD

The present invention relates to an insect pest-repellent film, an insect pest-repellent paint, which are directed toward preventing flying insects such as midges or planthoppers and are applied for lighting fixtures or the like, and improvement of a method for producing the same.

BACKGROUND ART

Conventionally, many insects have been attracted to lighting fixtures, and many contrivances have been provided as measures against this. In the case of an incandescent light, since the surface temperature of an envelope thereof is high and this light contains very little ultraviolet light, it attracts fewer insects when compared with a fluorescent light.

On the other hand, with lighting fixture, to enhance a decorative effect or to protect a luminescent part from moisture or dusts, a type in which a luminescent part, or light bulb is not exposed but covered with, for example, a rounded enclosure, envelope or a glove usually made of glass is broadly used. In this type of lighting fixture also, there are small holes or gaps between a glove part and a lighting fixture body, or at the top of the lighting fixture, in order to release heat of a luminescent part and so on. Small insects attracted to light come into a glove through these narrow spaces and die within several hours due to lack of water, or heat, and this causes contamination of the interior of the glove.

Conventionally, a structural attempt to diminish these narrow spaces to control insect invasion has repeatedly been made. However, since there is also a problem regarding release of heat generated inside, a decisive measure has not been proposed yet.

In respect of a method for controlling insect invasion into the enclosure of the above described lighting fixtures, it is desired that the problem be solved with consideration given to release of heat.

Moreover, since a lighting fixture may be installed at a high elevation because of its property, enormous efforts are needed for the maintenance of dead insects accumulated inside an enclosure thereof, and so a means of solving such a problem is required.

Furthermore, generally regarding insect-repellent techniques, volatile insect repellent agents have been studied and developed for the conservation of clothes or the like, and now these agents are commercially available.

However, since lighting fixtures are used in a living environment including a living room, taking into consideration that it may be absorbed through the expiratory air of humans, an agent with a high vapor pressure cannot be used. That is, differing from volatile insect repellent agents, lighting fixtures are in an environment where repellent techniques using stimulation on insect olfactory sense cannot be applied. Therefore, a safer repellent technique is strongly required.

DISCLOSURE OF THE INVENTION

The present invention is directed toward solving the above described problems, and an object of the present invention is to provide an insect pest-repellent film or the like to realize a safer repellent technique.

To achieve the above object, one aspect of the present invention is an insect pest-repellent film comprising an insect pest-repellent agent interspersed at intervals shorter than a landing part, when a flying insect having a body length of 1 to 6 mm lands.

Another aspect of the present invention is the insect pest-repellent film, wherein said insect pest-repellent agent is a porous carrier particle comprising a repellent ingredient and a surfactant.

Still another aspect of the present invention is the insect pest-repellent film, wherein said surfactant is located close to said repellent ingredient in said porous carrier particle.

Yet still another aspect of the present invention is the insect pest-repellent film, wherein said porous carrier particle is fixed to a substrate by a paint binder.

Still yet another aspect of the present invention is the insect pest-repellent film, wherein the particle size of said porous carrier particle is greater than the thickness of said paint binder.

A further aspect of the present invention is the insect pest-repellent film, wherein said repellent ingredient is infiltrated into said porous carrier particles.

A still further aspect of the present invention is the insect pest-repellent film, wherein said insect pest-repellent agent consists only of a repellent ingredient.

A yet further aspect of the present invention is the insect pest-repellent film, wherein said repellent ingredient is fixed to a substrate by a paint binder.

A still yet further aspect of the present invention is an insect pest-repellent paint comprising a porous carrier particle comprising a repellent ingredient and a surfactant;
a paint binder; and
a solvent.

An additional aspect of the present invention is the in sect pest-repellent paint, wherein said solvent is compatible with a paint substrate.

A still additional aspect is the insect pest-repellent paint, comprising a base coating material wherein said porous carrier particles are dispersed in said solvent, and
a facing material comprising said repellent ingredient.

A yet additional aspect of the present invention is the insect pest-repellent paint, wherein a surfactant is contained in at least either said base coating material or said facing material.

A still yet additional aspect of the present invention is the insect pest-repellent paint, wherein said porous carrier particle is silica gel.

A supplementary aspect of the present invention is the insect pest-repellent paint, wherein said porous carrier particle is an intercalation compound.

A still supplementary aspect of the present invention is the insect pest-repellent paint, wherein said intercalation compound is a hydrotalcite compound.

A yet supplementary aspect of the present invention is the insect pest-repellent paint, wherein the surface of said porous carrier particle is subjected to a hydrophobic treatment.

A still yet supplementary aspect of the present invention is the insect pest-repellent paint, wherein said surfactant is a nonionic surfactant.

Another aspect of the present invention is the insect pest-repellent paint, wherein said paint binder is water emulsion and said solvent is water.

Still another aspect of the present invention is a method for producing an insect pest-repellent paint comprising allowing a repellent ingredient, simultaneously with a surfactant, to be adsorbed and supported onto a porous carrier particle that is an inorganic oxide; and then allowing dispersion in a solvent comprising at least a paint binder.

The present invention as stated above includes, as a specific example of insect pest-repellent films, a structure in which both a porous carrier particle comprising a repellent ingredient and a surfactant located at least close to the repellent ingredient are fixed to a substrate by a paint binder.

Moreover, by way of example, the present invention as stated above is characterized in that it has at least cyclopropane carboxylate as a repellent ingredient, and comprises a structure in which porous carrier particles of inorganic oxides comprising at least the repellent ingredient, and surfactants located close to the repellent ingredient are dispersed in a paint layer. Or, it is characterized in that it has at least cyclopropane carboxylate as a repellent ingredient, and comprises at least a porous carrier particle, a surfactant and a solvent, and the solvent is compatible with a paint substrate. Furthermore, it is characterized in that it has a base coating material wherein the porous carrier particles of inorganic oxides are dispersed in the solvent compatible with the paint substrate, and a facing material comprising at least cyclopropane carboxylate as a repellent ingredient, and it is characterized in that at least either the base coating material or the facing material comprises the surfactant.

Herein, it is preferred that a repellent ingredient, cyclopropane carboxylate, contained in an insect pest-repellent paint is at least Cyphenothrin, a porous carrier particle is silica gel or a hydrotalcite compound, and further the surface of the porous carrier particle is subjected to a hydrophobic treatment. It is preferred that a surfactant contained in the insect pest-repellent paint is a nonionic surfactant.

Moreover, it is preferred that a paint binder contained in an insect pest-repellent paint is a water emulsion paint resin and a solvent is water.

Furthermore, it is characterized in that, 10 parts by weight to 500 parts by weight, in solid weight conversion, of paint binder is added with respect to 100 parts by weight of cyclopropane carboxylate that is a repellent ingredient contained in an insect pest-repellent paint.

A production method of the present invention is characterized in that it comprises allowing a repellent ingredient to be adsorbed and supported onto a porous carrier particle of an inorganic oxide and then allowing dispersion in a solvent comprising at least a paint binder.

It should be noted that the term close to" in the present invention refers to a negligible extent when compared with the size of a leg or antenna of insects that is in contact.

EXPLANATION OF SIGNS

Figure 1:
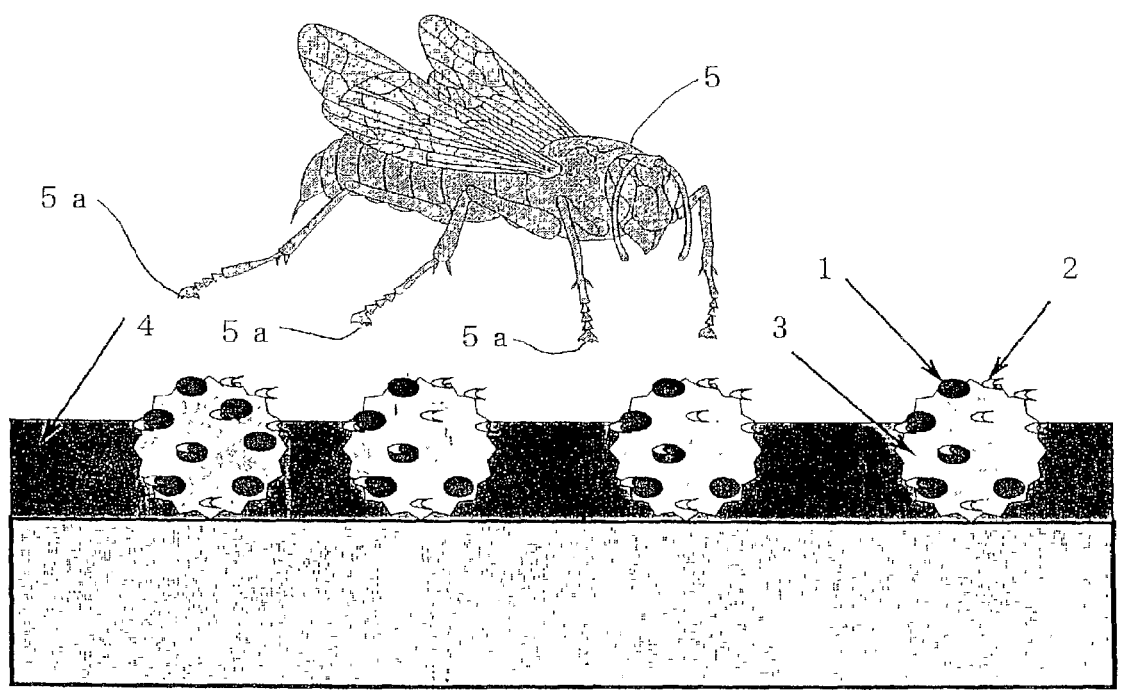
FIG. 1 is a figure explaining the operation principle the present invention.

1 Repellent ingredient
2 Surfactant
3 Porous carrier
4 Paint binder
5 Flying insect
5a Leg of flying insect

BEST MODE FOR CARRYING OUT THE INVENTION

In respect of insect invasion into lighting fixtures, a mechanism is considered, in which an insect that comes by flying (hereinafter referred to as flying insect) lands on the top of an enclosure or on a lighting fixture body, and thereafter the insect moves around the landing site and due to phototaxis, comes inside an enclosure by way of a connection part between the fixture and the glove, etc.

Thus, in the present invention, a contact repellent agent ingredient (hereinafter referred to as repellent ingredient) is located in a connection part between a lighting fixture body and an enclosure part, so that a flying insect moving around cutaneously absorbs the ingredient through its contact parts such as legs or antennas and then the excitement of nerve is transmitted to the brain, thereby causing the flying insect to remove itself from the site.

As a repellent ingredient used herein, cyclopropane carboxylate that is safer than conventional organophosphorus agents can be used. Of these, by using Cyphenothrin having a high contact repellent capability, a repellent effect can sufficiently be exerted.

Further, regarding use in a lighting fixture, heat resistance, weather resistance, and particularly ultraviolet light resistance are required. Regarding heat resistance, the temperature of a glove is always at room temperature or higher, that is, about 40° C., and so long-term durability is required. Moreover, since there are parts generating ultraviolet light such as a luminescent light tube inside a lighting fixture, weather resistance is required. Regarding these requirements, among cyclopropane carboxylate materials, relatively Cyphenothrin meets the requirements.

To exert the above described repellent effect with a minimum amount of a repellent ingredient, in respect of configuration methods for allowing a repellent ingredient to efficiently contact the skin of an insect, two methods will be explained.

Firstly, a method for applying a paint to locate a repellent ingredient in the above described part will be provided.

To keep a large contact face with the skin of a flying insect, asperities are provided on the surface of a paint film, and a repellent ingredient is located on the asperities. A method for producing asperities comprises dispersing porous carrier particles of inorganic oxides in a paint film and then producing asperities due to the volume.

Moreover, it is also possible to previously impregnate porous carrier particles of inorganic oxide with a repellent ingredient before dispersing the particles in a paint film.

Furthermore, it is also possible that porous carrier particles of inorganic oxide are previously located on what is called a paint substrate of a lighting fixture or glove as a base-coating process, and then the base coat is overcoated with a repellent ingredient.

On the other hand, to impregnate porous carrier particles of inorganic oxides with a repellent ingredient more easily, it is also possible that the surface of the porous carrier particles of inorganic oxides is subjected to a hydrophobic treatment. By performing this treatment, the capability of an oil-soluble repellent ingredient that is adsorbed and supported onto an originally hydrophilic porous carrier particle of inorganic oxide can be improved, and not only the absolute supported amount increases, but it also becomes possible to improve the persistence of a repellent effect due to improvement of the adsorption capability.

Still more, since a repellent ingredient is water-insoluble, it is also possible to reduce the amount of the repellent ingredient contained in a paint, while increasing the amount of the repellent ingredient adsorbed onto a carrier surface by using a water emulsion paint as a paint and water as a solvent.

Still further, as a method for locating a repellent ingredient on a glove surface, since the repellent ingredient implanted in a paint binder cannot be expected to exert an effect, it is possible that the repellent ingredient is dissolved in a solvent mutually soluble with a constitutive binder of the glove that is a substrate, without using the paint binder, and thereafter applied on the glove. That is to say, by applying the above described structure, the substrate binder on the glove surface swells after coating, and on swelling, the repellent ingredient attaches to the substrate surface, so that the repellent ingredient is allowed to locate on the surface of a substrate in conjunction with evaporation of the solvent.

Secondly, use of a surfactant as a synergist will be explained.

To allow the skin of a flying insect to efficiently absorb a repellent ingredient, a nonionic surfactant can be used. That is, by using the above surfactant, the above described repellent ingredient that is oil soluble can efficiently be transcribed to the cutaneous tissues of a flying insect from a repellent paint film, and so it is possible to effectively use a very small amount of repellent ingredient. That is, particularly regarding repellence of flying insects, the average body length of flying insects is short, the insects having a body length of less than 2 mm are also included, and in most cases the body length of the insects, which come into a glove by way of gaps and die inside the glove, is at longest 6 mm or shorter. Since the body weight of these flying insects is light and further legs and antennas thereof are thin and short, in many cases the combined use of the above described surfactant exerts improvement of a repellent effect.

These will be provided as a specific structure, and the operation principle will be explained with a figure.

In an insect pest-repellent film shown in FIG. 1, 1 denotes a repellent ingredient, 2 denotes a surfactant, 3 denotes a porous carrier, and 4 denotes a paint binder. Where a flying insect 5 contacts the surface of the insect pest-repellent film, a leg part 5*a* of the flying insect 5 touches the surface of the porous carrier 3 jutting from the paint film surface. Since the repellent ingredient 1 is supported on the porous carrier 3, and simultaneously the surfactant 2 is also supported thereon, the leg 5*a* of the flying insect contacts the surfactant 2 as well as the repellent ingredient 1. Because of the action of the surfactant 2, a very small amount of the repellent ingredient 1 is efficiently absorbed through the skin of the insect 5 and then skin stimulation generated there is transmitted to the brain of the flying insect 5, so that the flying insect 5 is induced to take an avoiding action.

(Embodiment 1)

As an agent having a contact repellent, among cyclopropane carboxylates, Cyphenothrin (α-cyano-3-phenoxybenzyl chrysanthemate) was selected in consideration of a safety standpoint or the like and used as a repellent ingredient. Using this repellent ingredient, a repellent paint having the following composition was prepared.

To obtain a repellent effect, 20 to 80 parts by weight of, in this embodiment, 50 parts by weight of Cyphenothrin, and 80 to 20 parts by weight of, in this embodiment, 50 parts by weight of Etofenprox were mixed to obtain a repellent ingredient.

As a sorbitan fatty acid ester type nonionic surfactant, 10 to 50 parts by weight of, here 50 parts by weight of sorbitan tristearate was added with respect to 100 parts by weight of repellent ingredient.

As a porous carrier particle of an inorganic oxide, a hydrotalcite compound having a high ability to support a repellent ingredient was used in this embodiment. As the properties of a carrier, a primary particle is a hexagonal plate crystal and these primary particles are laminated as an intercalation compound to form secondary particles, and there was used a material having, as the primary particle size, a plate diameter of 0.3 μm, a thickness of 0.06 μm and a specific surface area of 14 $m^2/g$, the secondary particle having a diameter of several tens of μm. With respect of 100 parts by weight of this repellent ingredient, 50 parts by weight of carrier was fully mixed, dispersed and then used, and thereby the insect pest-repellent agent of the present invention was prepared.

Next, regarding a paint, where an acryl binder was used as a glove substrate, there was used an acryl paint obtained by solubilizing the acryl binder using an organic solvent such as toluene or butyl acetate, and 10 to 500 parts by weight, in this embodiment, 30 parts by weight in solid binder weight conversion, was added with respect to 100 parts by weight of repellent ingredient. Then, the above described insect pest-repellent agent was mixed thereto using a butyl acetate solvent and thereafter the mixture was prepared to have a viscosity capable of being applied with a spray, and thereby the insect pest-repellent paint of the present invention was prepared.

This paint was applied with a spray to the gap of a connection part between a glove part and a lighting fixture body of a lighting fixture at a concentration of 0.2 g/1 $m^2$ in repellent ingredient conversion, to form the insect pest-repellent paint of the present invention. In this embodiment, in a case where the thickness of an insect pest-repellent film is set at 3 μm, where the diameter of a secondary particle is 30 μm, the secondary particles are interspersed at intervals of 53 μm on the film, and where the diameter is 10 μm, these particles are interspersed at intervals of 10 μm thereon. At this time, for the reason that the diameter of the secondary particle is greater than the thickness of the paint, the secondary particle juts from the surface of a paint film, when the film is formed.

At this time, assuming that a flying insect is an insect of Diptera such as a midge, where the dimension is 2 mm, the length of one side of the area where a leg contacts with the insect pest-repellent film is about 150 to 300 μm. In the case of an insect smaller than this, e.g. an insect having a body length of about 1 mm, the length of one side as stated above is about 75 to 150 μm, and this means that secondary particles are interspersed at intervals smaller than a landing site, when a flying insect lands on a film face using the legs, antennas or the like.

Accordingly, once a flying insect lands on an insect pest-repellent film containing secondary particles interspersed at intervals as stated above, somewhere in its landing part is inevitably in contact with the secondary particles jutting from the surface of the insect pest-repellent film. Through the medium of the landing part, it becomes possible to allow a repellent ingredient penetrated into the secondary particles to reach the skin of the flying insect.

Moreover, addition of a carrier to a repellent ingredient enables to extend the area where a flying insect is in contact with the repellent ingredient and to allow the insect to efficiently absorb a minimum amount of the repellent ingredient.

Furthermore, a high concentration of repellent ingredient is interspersed in a paint film by allowing the repellent ingredient to be supported on a carrier, and thereby it is possible to give a stronger stimulation to the sense organ of an insect. This effect is similar to an action that when food containing dispersed salt grains is provided to human tongue, the tongue tastes more salty than when it tastes food having the same salt concentration, and so this has an effect of further strengthening a repellent action.

Evaluation of the insect repellent capability of such an insect pest-repellent film was carried out as follows.

As evaluation of an insect repellent capability, using a 70W round shape luminescent light fixture, the fixture was placed in the open with no rain, the light stayed on from 17:00 in the evening to 5:00 in the morning on the following day in the summer season, and the number of flying insects come into a glove was counted. The sample of this embodiment and the same fixture with no repellent treatment were placed keeping a distance of 3 m or more from each other.

To evaluate the effect of paint ingredients on a repellent capability, on a basis of composition in the embodiment of the present invention, there were prepared several types of sample, the value of the constituents of which were altered, and the same evaluation was carried out.

In this test, where the number of flying insects come into an untreated zone on which a fixture with no repellent treatment was grounded, was from twice or more to less than 10 times of the number of flying insects come into a glove with a repellent treatment zone on which the sample of the present invention was grounded, it is represented by , and where the number is more than 10 times, it is represented by O.

Results of the evaluation are shown in (Table 1).

(Embodiment 2)

In the composition of a paint similar to Embodiment 1, there was used silica gel (average particle diameter: 1 μm) (trade name: SYLOPHOBIC 200) as a porous carrier particle of an inorganic oxide, the surface of which was subjected to a hydrophobic treatment. In respect of this paint also, an evaluation test was carried out in the same manner as in Embodiment 1 to confirm a repellent capability.

(Embodiment 3)

As an agent having a contact repellent, 50 parts by weight of Cyphenothrin and 50 parts by weight of Etofenprox were mixed to prepare a repellent ingredient. To this, 50 parts by weight of sorbitan tristearate was added with respect to 100 parts by weight of the repellent ingredient.

As a porous carrier particle of an inorganic oxide, 50 parts by weight of carrier that is a hydrotalcite compound was fully mixed, dispersed and used with respect to 100 parts by weight of repellent ingredient.

To these ingredients, there was added a solvent having toluene as a main ingredient, which has a mutual solubility with a glove substrate that is an acryl binder, so that a paint was prepared to have a viscosity capable of being applied with a spray.

This paint was applied with a spray to a connection part between a glove and a lighting fixture body, and the repellent rate was evaluated by comparing with an untreated sample.

As a result, a practical repellent capability was confirmed.

(Embodiment 4)

As an agent having a contact repellent, 50 parts by weight of Cyphenothrin and 50 parts by weight of Etofenprox were mixed to prepare a repellent ingredient.

As a porous carrier particle of an inorganic oxide, 50 parts by weight of carrier that is a hydrotalcite compound was

TABLE 1

| | Repellent ingredient | | Carrier (per 100 parts by weight of | Surfactant (per 100 parts by weight of | Paint binder (per 100 parts by weight of | Repellent | |
|---|---|---|---|---|---|---|---|
| | Cyphenothrin | Etofenprox | ingredient) | ingredient) | ingredient) | capability | Remarks |
| (1) | 20 | 80 | 50 | 50 | 30 | o | having surface viscosity |
| (2) | 50 | 50 | 50 | 50 | 30 | o | |
| (3) | 80 | 20 | 50 | 50 | 30 | o | having insecticidity |
| (4) | 50 | 50 | 50 | 500 | 30 | Δ | |
| (5) | 50 | 50 | 50 | 10 | 30 | Δ | |
| (6) | 50 | 50 | 50 | 50 | 10 | o | having surface viscosity |
| (7) | 50 | 50 | 50 | 50 | 500 | Δ | |

In Table 1, the present embodiment represented by No. (2) exhibited the best effect. Nos. (4), (5) and (7) did not obtain a sufficient repellent capability when compared with No. (2). Nos. (1) and (6) obtained a sufficient repellent capability, but since the paint film surfaces thereof have viscosity, there is a fear that dusts or the like attach thereto and contaminate a fixture. Since No. (3) has an excessively strong repellent capability, there is a fear that it kills flying insects and thereby contaminates inside the fixture.

Therefore, in each example listed above, it can be said that Nos. (2), (4) and (5) are compositions suitable for practical use.

fully mixed and dispersed with respect to 100 parts by weight of repellent ingredient.

As a paint, carrier particles impregnated with the above described repellent ingredient were dispersed in an aqueous paint containing an acryl paint binder dispersed as emulsion, and water was further added thereto to control viscosity, thereby preparing a paint used in application with a spay.

This paint was applied with a spray to a connection part between a glove and a lighting fixture body, and the repellent rate was evaluated by comparing with an untreated sample.

As a result, a practical repellent capability was confirmed.

(Embodiment 5)

A solvent having toluene as a main ingredient, which has a mutual solubility with a glove substrate that is an acryl binder, was added to porous carrier particles of inorganic oxides and the mixture was prepared to a viscosity capable of being applied with a spay.

This base coating material was applied with a spray to a connection part between a glove and a lighting fixture body. After application of the material, air drying was carried out followed by heat drying at a temperature of about 80° C., so that a carrier was fixed on the glove in a layer form.

The top of the base-coated layer was overcoated with a repellent ingredient. As an agent having a contact repellent, 50 parts by weight of Cyphenothrin and 50 parts by weight of Etofenprox were mixed to prepare the repellent ingredient. To this, 50 parts by weight of a glycerin fatty acid ester type surfactant, glycerol monooleate, was added as a nonionic surfactant, with respect to 100 parts by weight of the repellent ingredient.

To these ingredients, there was added a solvent having toluene as a main ingredient, which has a mutual solubility with a glove substrate that is an acryl binder, so as to prepare a facing material having a viscosity capable of being applied with a spray.

This paint was applied with a spray to a connection part between the same glove that was base-coated and a lighting fixture body, and the repellent rate was evaluated by comparing with an untreated sample.

As a result, a practical repellent capability was confirmed.

The above stated embodiments of the present invention have an effect of controlling flying insects having a short body length and a light body weight, where a paint obtained by adding a carrier and a surfactant to the above described repellent ingredient is used for insect repellency of light fixtures.

Moreover, a combined use of a repellent ingredient and a surfactant has an effect of enhancing absorption efficiency that the ingredient is absorbed through the skin of an insect. Since a minimum amount of repellent ingredient can be used effectively by this combined use, it has an effect of improving the persistence of a repellent effect.

Furthermore, by using an ingredient having a contact repellent effect and high heat- and ultraviolet light-resistance as a repellent agent, the heat resistance of the repellent agent can be improved in a heat processing, and further there is no influence on the repellent performance then. This enables to control reduction of the repellent agent by decomposition or the like, when a heat processing is carried out after application of the repellent agent, and this does not only impair the repellent capability, but also has a great effect for keeping influence on operators or environment to a minimum. It can also be expected that the persistence of a repellent effect is improved, even when the agent is used in a lighting fixture having a large amount of ultraviolet light exposure at a relatively high temperature in the usage environment.

It should be noted that, in the above described embodiments, as a flying insect, a midge of Diptera was used as an example and explained, but there may also be applied other insects of Diptera, insects of Hemiptera such as a planthopper or leafhopper, or insects of Lepidoptera such as a moth. In short, the flying insects in the present invention are any insect to the extent that the insects have a body length of 1 mm to 6 mm, and are not limited to type.

Moreover, in the above described embodiments, the insect pest-repellent film of the present invention has been explained, in which secondary particles comprising repellent ingredient-supported carrier particles are interspersed in a paint film as a insect pest-repellent agent, but the insect pest-repellent agent of the present invention may also be realized with a structure that the repellent ingredient is directly interspersed on the paint film.

Industrial Applicability

As is clear from what is described as above, according to the present invention, a safer repellent technique suitable for lighting fixtures can be provided by using stimulation on the touch sense of flying insects.

The invention claimed is:

1. A method for producing an insect pest-repellent paint of an insect pest repellent film of a lighting fixture, the method comprising:

allowing a contact pest-repellent ingredient that is cutaneously absorbed by contact by a flying insect and causes the flying insect to leave without killing said insect, simultaneously with a surfactant, to be adsorbed and supported onto porous carrier particles of a hydrotalcite compound;

then dispersing said porous carrier particles in a solvent comprising at least a paint binder, and spraying the solvent comprising the dispersed porous carrier particles onto a gap of a connection part between a glove part and a lighting fixture body of a lighting fixture and forming said insect pest repellent film of a lighting fixture; such that:

said porous carrier particles are intersperced at intervals shorter than a landing site, when a flying insect having a body length of 1 to 6 mm lands on said film of said insect repellent paint; and said porous carrier particles are thicker than said insect repellent paint.

2. The method of claim 1, wherein said surfactant is a nonionic surfactant.

3. The method of claim 1 wherein said repellent ingredient is a α-cayno-3-phenoxybenzyl chrysanthemate.

4. The method of claim 3, wherein said surfactant is a nonionic surfactant.

5. The method of claim 4, wherein said paint binder is water emulsion and said solvent is water.

* * * * *

UNITED STATES PATENT AND TRADEMARK OFFICE
CERTIFICATE OF CORRECTION

PATENT NO. : 7,041,306 B2
APPLICATION NO. : 10/129943
DATED : May 9, 2006
INVENTOR(S) : Toshikazu Tomioka et al.

It is certified that error appears in the above-identified patent and that said Letters Patent is hereby corrected as shown below:

On the title Page, ABSTRACT item [57], should read:

Insects come into lighting fixtures, and enormous efforts are expended to clean the interior of an enclosure. There is provided a repellent paint, which prevents this and has a prolonged repellent effect.
    The repellent paint is characterized in that it has at least cyclopropane carboxylate as a repellent ingredient, and comprises at least a porous carrier particle of an inorganic oxide, a surfactant, a paint binder and a solvent.

At Column 10, line 26 in claim 1, "allowing a contact pest-repellent ingredient" should read --allowing a contact insect pest-repellent ingredient--.

At Column 10, line 43 in claim 1, "thicker than said insect repellent" should read --thicker than said film of said insect repellent--.

Signed and Sealed this

Twenty-sixth Day of December, 2006

JON W. DUDAS
*Director of the United States Patent and Trademark Office*